(12) United States Patent
Morhain et al.

(10) Patent No.: US 12,233,187 B2
(45) Date of Patent: Feb. 25, 2025

(54) VOLATILE SUBSTANCE DIFFUSER

(71) Applicant: ZOBELE HOLDING S.P.A., Trento (IT)

(72) Inventors: Cedric Morhain, Barcelona (ES); Joaquim Llorente Alonso, Barcelona (ES); Alba Graus Ferrer, Barcelona (ES)

(73) Assignee: ZOBELE HOLDING S.P.A., Trento (IT)

( * ) Notice: Subject to any disclaimer, the term of this patent is extended or adjusted under 35 U.S.C. 154(b) by 0 days.

(21) Appl. No.: 16/958,201

(22) PCT Filed: Dec. 27, 2018

(86) PCT No.: PCT/EP2018/097031
§ 371 (c)(1),
(2) Date: Jun. 26, 2020

(87) PCT Pub. No.: WO2019/129814
PCT Pub. Date: Jul. 4, 2019

(65) Prior Publication Data
US 2020/0360556 A1     Nov. 19, 2020

(30) Foreign Application Priority Data

Dec. 28, 2017   (ES) .................. ES201731487

(51) Int. Cl.
*A61L 9/012*         (2006.01)
*A61L 9/04*          (2006.01)
(Continued)

(52) U.S. Cl.
CPC .............. *A61L 9/012* (2013.01); *A61L 9/042* (2013.01); *A61L 9/20* (2013.01); *B01J 13/02* (2013.01)

(58) Field of Classification Search
CPC . A61L 9/012; A61L 9/042; A61L 9/20; A61L 9/125; A61L 9/127; A61L 2209/13; B01J 13/02; D06M 13/005; D06M 23/12
See application file for complete search history.

(56) References Cited

U.S. PATENT DOCUMENTS 5,109,029 A    4/1992  Malone
5,734,590 A    3/1998  Tebbe
(Continued)

FOREIGN PATENT DOCUMENTS

DE      4305141 A1 *  8/1994  ............. A61L 9/125
EP      1 410 753 A1    4/2004
(Continued)

OTHER PUBLICATIONS

International Search Report received for PCT Patent Application No. PCT/EP2018/097031 mailed on Jun. 4, 2019, 5 page.

(Continued)

*Primary Examiner* — Sean E Conley
*Assistant Examiner* — Brendan A Hensel
(74) *Attorney, Agent, or Firm* — Amster, Rothstein & Ebenstein LLP

(57) ABSTRACT

The volatile substance diffuser comprises a support (1) impregnated with the volatile substances, wherein at least one portion of the volatile substances is contained in at least first microcapsules (2) and second microcapsules (3) comprising a core (10) and a coating (11), the diffusion times of the first and second microcapsules (2, 3) being different to each other.
It enables the diffusion time of the volatile substances to be increased.

11 Claims, 2 Drawing Sheets

(51) Int. Cl.
*A61L 9/20* (2006.01)
*B01J 13/02* (2006.01)

(56) References Cited

U.S. PATENT DOCUMENTS

| | | |
|---|---|---|
| 6,375,983 B1 | 4/2002 | Kantor et al. |
| 2007/0196410 A1* | 8/2007 | Jadhav .................... B01J 13/02 424/408 |
| 2011/0094934 A1 | 4/2011 | Kundinger, Jr. |
| 2014/0371129 A1 | 12/2014 | Allison et al. |
| 2018/0243717 A1* | 8/2018 | Macedo Tavares ..... B01J 13/16 |

FOREIGN PATENT DOCUMENTS

| | | |
|---|---|---|
| WO | 2001/093814 A2 | 12/2001 |
| WO | 2016/124746 A1 | 8/2016 |
| WO | 2017/161364 A1 | 9/2017 |

OTHER PUBLICATIONS

Written Opinion received for PCT Patent Application No. PCT/EP2018/097031, 10 page.

Yamamoto, Takao & Koike, Michiru & Dobashi, Toshiaki. Melting and Swelling Behaviors of UV-Irradiated Gelatin Gel Microcapsules. Langmuir: the ACS journal of surfaces and colloids. vol. 23, No. 16, pp. 8531-8537 (2007).

* cited by examiner

VOLATILE SUBSTANCE DIFFUSER

CROSS-REFERENCE TO RELATED APPLICATIONS

This application is a National Stage entry under 35 U.S.C. 371 of International Patent Application No. PCT/EP2018/097031, filed on Dec. 27, 2018, which claims priority from Spanish Patent Application No. P201731487, filed Dec. 28, 2017, the entire contents of each of which are incorporated by reference herein.

FIELD

The present invention relates to a volatile substance diffuser, which comprises a support impregnated with volatile substances, which enables the diffusion time of the volatile substances to be increased.

BACKGROUND OF THE INVENTION

Volatile substance diffusers or simple air fresheners with impregnated supports are, despite innovations made in recent years, still the most popular air freshener, especially for small spaces, such as changing rooms or vehicles.

These diffusers generally consist of a support, for example, made of cardboard, with sufficient absorption capacity to contain the volatile substances that provide a specific fragrance, impregnated with said volatile substances and with some feature for hanging the device from a support.

Like any open system, the tendencies to evaporate or diffuse over the life of the product are consistently diminished, since the most volatile portion of the fragrance evaporates more quickly and only the least volatile portion of the fragrance remains after a certain amount of time.

The effect on the performance of the product is that, at this time, the intensity is lower and the fragrance is not so similar to the original fragrance. This reduction in the intensity of the fragrance and this change in aromatic notes occur over the life of the product.

Some alternative solutions have been proposed to improve this behaviour. If we disregard the cases in which the support comes in contact with a receptacle containing the volatile substances that will evaporate over the life of the product, which in the end is similar to systems with a wick, the remaining existing systems have multiple receptacles, which are activated, generally manually, in order to successively release a new dose of the original fragrance.

For example, there are systems with multiple receptacles closed by a thin film that is punctured with some needles when the user so desires, the liquid then simply flows into the support and is then freely evaporated, with the typical breakdown of the open system but to a lesser extent, since the life of the product is divided into a succession of repeated single doses.

In some cases, this activation of the multiple doses can be automated thanks to some mechanical and/or electronic devices, to prevent the user from needing to activate the multiple doses.

As a result, now there are only two solutions for a simple diffuser with long-lasting intensity and consistency:
- any system in which the user has to manually activate multiple doses; or
- systems where an electronic system activates the multiple doses.

In both cases, the product is no longer simple, since in the first case it must be regularly handled by the user, and in the second case, the presence of electronic components increases the cost of the product and places it in a completely new and different category of products.

Therefore, an object of the present invention is to provide a volatile substance diffuser that is very simple and that enables the diffusion time of the volatile substances to be increased.

SUMMARY OF THE INVENTION

The volatile substance diffuser of the invention resolves the aforementioned drawbacks and has other advantages which are described below.

The volatile substance diffuser according to the present invention comprises a support impregnated with the volatile substances, and is characterised in that at least one portion of the volatile substances is contained in at least first microcapsules and second microcapsules comprising a core and a coating, the diffusion times of the first and second microcapsules being different to each other.

Thanks to this characteristic, the diffusion of the volatile substances is prolonged over time, since a portion of the volatile substances spreads after the diffusion of the other portion of the volatile substances.

Advantageously, the first and second microcapsules have different sizes, the ratio of the coating to the core is different for the first and second microcapsules, and/or the thickness of the coating is different for the first and second microcapsules.

Preferably, the support comprises a plurality of microcapsules different to each other.

The microcapsules can be activated to release the volatile substances thereof by means of mechanical tension, ultraviolet light and/or a change in pH.

According to a preferred embodiment, the support is made of cellulose, for example, compact cardboard.

BRIEF DESCRIPTION OF THE DRAWINGS

For the purpose of helping to make the foregoing description more readily understandable, it is accompanied by a set of drawings which, schematically and by way of illustration and not limitation, represent an embodiment.

DESCRIPTION OF A PREFERRED EMBODIMENT

As shown in the figures, the volatile substance diffuser according to the present invention is formed from a support 1, by way of a sheet impregnated with the volatile substances. Said support 1 can be made of any suitable material, although preferably it is made of cellulose, for example, compact cardboard.

Said volatile substances are contained, at least in part, in microcapsules, which are of at least two different types: first microcapsules 2 and second microcapsules 3.

Figure 1:
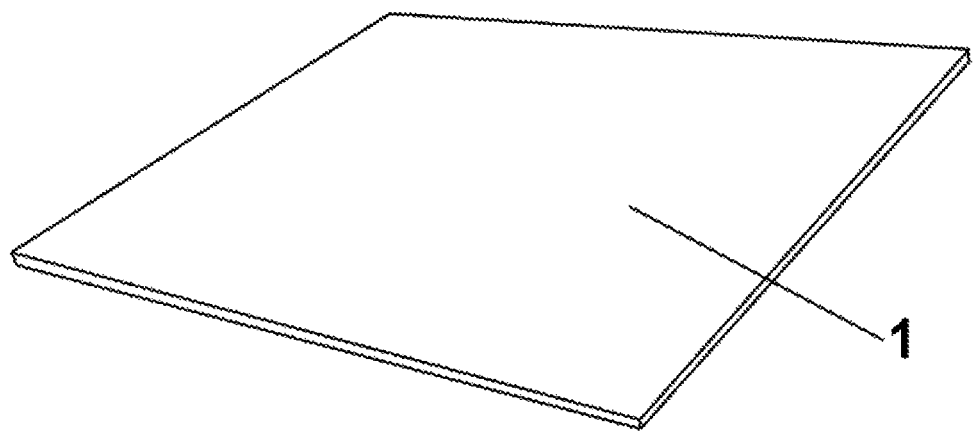
FIG. 1 is a perspective view of the volatile substance diffuser according to the present invention.
Figure 2:
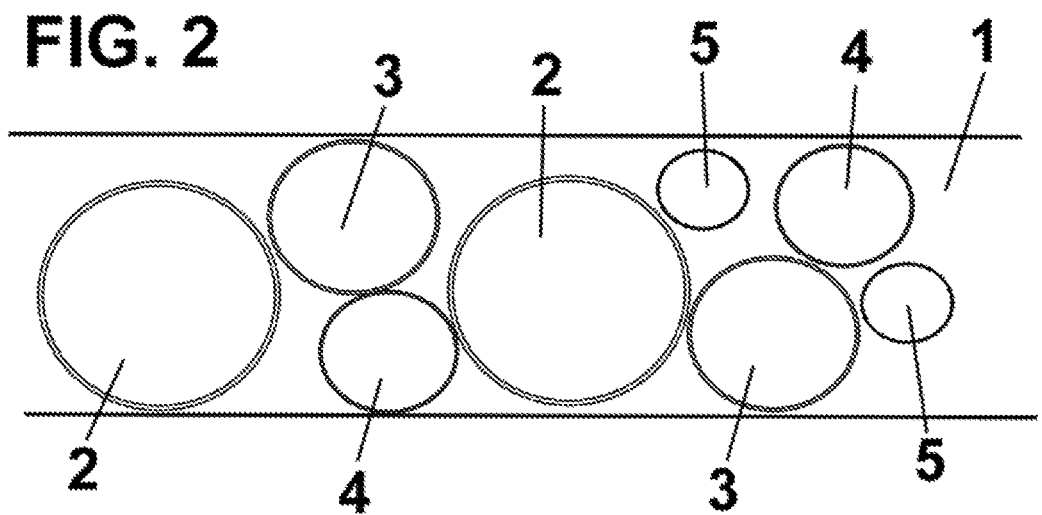
FIG. 2 is a schematic detailed view of the structure of the support forming the volatile substance diffuser according to the present invention, wherein the different types of volatile substances can be seen.

In the embodiment shown, the support 1 comprises four different types of microcapsules, identified with the reference numbers 2 to 5, as shown schematically in FIG. 2.

Said microcapsules are different because they have diffusion times different to each other in order to maximise the diffusion time of the volatile substances.

Figure 3:
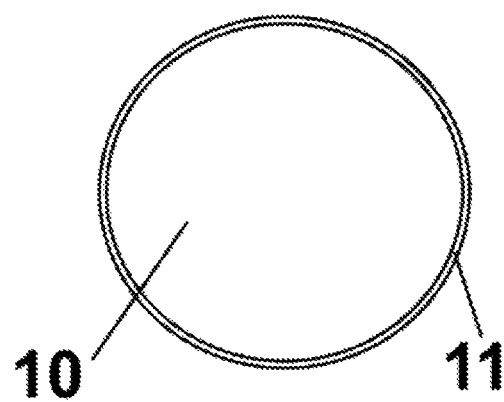
FIG. 3 is a transverse cross-sectional view of a microcapsule that is used in the volatile substance diffuser according to the present invention.

As can be seen in FIG. 3, each microcapsule comprises a core 10 and a coating 11, defining a substantially spherical shape.

The diffusion times thereof can be varied in different ways, for example, by changing the size of the microcapsules, the ratio of the core to the coating and/or the thickness of the coating.

It must be noted that the volatile substances can be contained in their entirety in the microcapsules, or they can combine freely impregnated volatile substances (without being contained in microcapsules) in the support and volatile substances contained in microcapsules with different diffusion times.

For the sale thereof, the diffuser according to the present invention is housed inside a sealed cover, to prevent any type of diffusion. Said sealed cover is removed when there is a desire to use the diffuser.

Upon removing the sealed cover, the freely impregnated volatile substances in the support 1, if any, will begin to spread to the environment. The remaining volatile substances contained in the microcapsules will not spread immediately, but will begin to diffuse with a delay when they are activated.

Said activation can be carried out in different ways. For example, they can be activated by means of mechanical tension, ultraviolet light and/or a change in pH.

Thus, it ensures that the diffusion of the volatile substances lasts longer than in a conventional diffuser wherein all the volatile substances spread at the same time.

Despite the fact that reference has been made to a specific embodiment of the invention, it is evident for the person skilled in the art that numerous variations and changes may be made to the volatile substance diffuser described, and that all the aforementioned details may be substituted by other technically equivalent ones, without detracting from the scope of protection defined by the attached claims.

The invention claimed is:

1. A volatile substance diffuser, comprising a support impregnated with volatile substances, wherein:
   at least a portion of the volatile substances is contained in at least one or more first microcapsules and one or more second microcapsules,
   each of the one or more first microcapsules and the one or more second microcapsules comprises a core and a coating,
   the one or more first microcapsules and the one or more second microcapsules are configured to have respective diffusion times that are different to each other such that, when the one or more first microcapsules and the one or more second microcapsules are activated simultaneously to release the volatile substances thereof, the one or more second microcapsules will begin to diffuse at a predetermined time after the diffusion time of the one or more first microcapsules to prolong the diffusion time of the volatile substances; and
   the first and second microcapsules are activated by ultraviolet light.

2. The volatile substance diffuser according to claim 1, wherein the one or more first microcapsules and the one or more second microcapsules have different sizes from one another.

3. The volatile substance diffuser according to claim 1, wherein a ratio of the coating to the core is different for the one or more first microcapsules and the one or more second microcapsules.

4. The volatile substance diffuser according to claim 1, wherein a thickness of the coating is different for the one or more first microcapsules and the one or more second microcapsules.

5. The volatile substance diffuser according to claim 1, wherein the support further comprises a plurality of additional microcapsules that are different to each other.

6. The volatile substance diffuser according to claim 1, wherein the support is made of cellulose.

7. A volatile substance diffuser, comprising a support impregnated with volatile substances, wherein:
   at least a portion of the volatile substances is contained in at least one or more first microcapsules and one or more second microcapsules,
   each of the one or more first microcapsules and the one or more second microcapsules comprises a core and a coating, and
   the one or more first microcapsules and the one or more second microcapsules are configured to have respective diffusion times that are different to each other such that, when the one or more first microcapsules and the one or more second microcapsules are activated simultaneously to release the volatile substances thereof, the one or more second microcapsules will begin to diffuse at a predetermined time after the diffusion time of the one or more first microcapsules to prolong the diffusion time of the volatile substances;
   wherein the support is impregnated with volatile substances that are not contained in the one or more first microcapsules and the one or more second microcapsules.

8. The volatile substance diffuser according to claim 7, wherein the volatile substances that are not contained in the one or more first microcapsules and the one or more second microcapsules begin to diffuse before the diffusion times of the one or more first microcapsules and the one or more second microcapsules.

9. The volatile substance diffuser according to claim 7, wherein the one or more first microcapsules and the one or more second microcapsules are activated to release the volatile substances thereof by mechanical tension.

10. The volatile substance diffuser according to claim 7, wherein the one or more first microcapsules and the one or more second microcapsules are activated to release the volatile substances thereof by ultraviolet light.

11. The volatile substance diffuser according to claim 7, wherein the one or more first microcapsules and the one or more second microcapsules are activated to release the volatile substances thereof by a change in pH.

* * * * *